(12) United States Patent
Sette et al.

(10) Patent No.: US 10,835,137 B2
(45) Date of Patent: Nov. 17, 2020

(54) SENSOR ARRANGEMENT AND CATHETER COMPRISING A SENSOR ARRANGEMENT

(71) Applicant: MEDYRIA AG, Winterhur (CH)

(72) Inventors: Mauro Massimo Sette, Winterhur (CH); Anita Di Iasio, Winterhur (CH)

(73) Assignee: MEDYRIA AG, Winterhur (CH)

( * ) Notice: Subject to any disclaimer, the term of this patent is extended or adjusted under 35 U.S.C. 154(b) by 0 days.

(21) Appl. No.: 16/075,140

(22) PCT Filed: Feb. 3, 2017

(86) PCT No.: PCT/EP2017/052352
§ 371 (c)(1),
(2) Date: Aug. 2, 2018

(87) PCT Pub. No.: WO2017/134206
PCT Pub. Date: Aug. 10, 2017

(65) Prior Publication Data
US 2018/0368702 A1    Dec. 27, 2018

(30) Foreign Application Priority Data
Feb. 4, 2016    (DE) .................. 10 2016 001 250

(51) Int. Cl.
*A61B 5/026*        (2006.01)
*G01F 1/684*        (2006.01)
(Continued)

(52) U.S. Cl.
CPC ............ *A61B 5/026* (2013.01); *A61B 5/6852* (2013.01); *G01F 1/684* (2013.01); *G01F 1/69* (2013.01);
(Continued)

(58) Field of Classification Search
CPC ........... A61B 5/02; A61B 5/026; A61B 5/027; A61B 5/6852; A61B 2562/043;
(Continued)

(56) References Cited

U.S. PATENT DOCUMENTS 3,900,819 A  *  8/1975  Djorup .................... G01F 1/692
                                                          338/320
4,453,405 A     6/1984  Zemel
(Continued)

FOREIGN PATENT DOCUMENTS

CN        1318147 A    10/2010
EP        0313120 A1   4/1989
(Continued)

OTHER PUBLICATIONS

Bradbury, LJS. "The Pulsed Wire Anemometer: Review and Further Developments" J. Braz. Soc. Mech. Sci. vol. 22, No. 1. 2000. (Year: 2000).*

(Continued)

*Primary Examiner* — Meredith Weare
(74) *Attorney, Agent, or Firm* — Straub & Straub; Michael P. Straub; Stephen T. Straub (57) ABSTRACT

A sensor arrangement including at least two displaced first sensors arranged in parallel in a first plane and adapted to measure a quantity of a fluid flow and a control unit adapted to determine, from the measured quantity of the fluid flow, information indicating at least a range of directions of the fluid flow in two dimensions.

11 Claims, 11 Drawing Sheets

(51) Int. Cl.
*A61B 5/00* (2006.01)
*G01P 5/12* (2006.01)
*G01F 1/69* (2006.01)

(52) U.S. Cl.
CPC ........ *G01P 5/12* (2013.01); *A61B 2562/0271* (2013.01); *A61B 2562/043* (2013.01)

(58) Field of Classification Search
CPC ..... A61B 2562/0271; G01P 5/00; G01P 5/10; G01P 5/12; G01F 1/00; G01F 1/68; G01F 1/684; G01F 1/688; G01F 1/696
See application file for complete search history.

(56) References Cited

U.S. PATENT DOCUMENTS

| | | | | |
|---|---|---|---|---|
| 4,483,200 | A * | 11/1984 | Togawa | G01F 1/7044 |
| | | | | 73/204.25 |
| 4,637,253 | A | 1/1987 | Sekimura et al. | |
| 6,234,016 | B1 * | 5/2001 | Bonne | G01F 1/6845 |
| | | | | 73/204.26 |
| 6,502,459 | B1 * | 1/2003 | Bonne | G01F 1/6845 |
| | | | | 73/170.11 |
| 6,871,535 | B2 * | 3/2005 | Blakley | A61M 15/009 |
| | | | | 73/204.21 |
| 9,400,197 | B2 * | 7/2016 | Najafi | G01F 1/69 |
| 2002/0100316 | A1 | 8/2002 | James et al. | |
| 2012/0316419 | A1 * | 12/2012 | Chevalier | A61B 5/02007 |
| | | | | 600/381 |
| 2014/0336476 | A1 * | 11/2014 | Li | A61B 5/026 |
| | | | | 600/301 |
| 2015/0253169 | A1 | 9/2015 | Najafi et al. | |

FOREIGN PATENT DOCUMENTS

| | | |
|---|---|---|
| WO | 2011101813 A1 | 8/2011 |
| WO | 2014186912 A1 | 11/2014 |

OTHER PUBLICATIONS

Notification of Transmittal of the International Search Report and the Written Opinion of the International Searching Authority, or the Declaration containing the International Search Report and the Written Opinion of the International Searching Authority from PCT/EP2017/052352 dated Apr. 11, 2017, pp. 1-10.

Search report from priority application DE 102016001250.1, 2 pages.

English translation and Chinese language version of State of Intellectual Property Office of China, First Office Action from Chinese Application No. 201780009488.6, dated Mar. 15, 2019, pp. 1-7.

State of Intellectual Property Office of China, Second Office Action from Chinese Application No. 201780009488.6, Chinese Office Action dated Sep. 9, 2019, pp. 1-7.

* cited by examiner

-- Prior Art --

| $g(ES_{max}, ES_{min})$ | $U$ | | |
|---|---|---|---|
| | $V_1$ | $V_2$ | $V_3$ |
| $\vartheta_1$ | $(ES_{max}, ES_{min})_{1,1}$ | $(ES_{max}, ES_{min})_{1,2}$ | $(ES_{max}, ES_{min})_{1,3}$ |
| $\vartheta_2$ | $(ES_{max}, ES_{min})_{2,1}$ | $(ES_{max}, ES_{min})_{2,2}$ | $(ES_{max}, ES_{min})_{2,3}$ |
| $\vartheta_3$ | $(ES_{max}, ES_{min})_{3,1}$ | $(ES_{max}, ES_{min})_{3,2}$ | $(ES_{max}, ES_{min})_{3,3}$ |

Fig.6

SENSOR ARRANGEMENT AND CATHETER COMPRISING A SENSOR ARRANGEMENT

The present disclosure generally relates to the field of sensor technology. More specifically, the present disclosure relates to a sensor arrangement and a catheter comprising a sensor arrangement.

A sensor able to measure a velocity of a fluid flow along two directions may be needed in certain cardiovascular procedures. In the state of the art, this is obtained by using two perpendicular sensors in order to obtain the direction of the fluid flow, often described by an incidence angle $\vartheta$.

In order to measure the velocity of the fluid flow in three dimensions, three orthogonal displaced sensors are needed. A measurement of the velocity of the fluid flow in two dimensions requires a sensor arrangement with two orthogonal displaced sensors.

In order to correctly measure the velocity of the fluid flow, the two sensors should be subject to the same velocity and the fluid flow should exchange the same amount of heat with the sensor.

In case a hot film or hot wire is used with a catheter, the catheter should be linked to a round surface of the sensor and it is possible that the surface of the two sensors being exposed to the flow will be different. For example, the horizontal sensor could be placed around the catheter while the vertical sensor could lie on one side. With this configuration both sensors cannot be exposed to the same flow when the sensor touches a vessel wall and only a part of the sensor is covered by the fluid flow.

A possible solution would be to minimize the sensor's surface, but this would also minimize the sensor's sensibility.

Therefore, a space-saving solution for a sensor arrangement is needed ideally not limiting the sensor's sensibility.

Accordingly, there is a need for an improved sensor arrangement and a catheter comprising such a sensor arrangement.

According to a first aspect, a sensor arrangement is provided. The sensor arrangement comprises at least two displaced first sensors and a control unit. The at least two displaced first sensors are arranged in parallel in a first plane and are adapted to measure a quantity of a fluid flow. The control unit is adapted to determine, from the measured quantity of the fluid flow, information indicating at least a range of directions of the fluid flow in two dimensions.

In other words, the at least two sensors are arranged parallel to one another/in parallel to each other. Further, the at least two sensors are displaced from each other. The term fluid flow can be understood as flow of a/the fluid.

The term at least a range of directions of the fluid flow may relate to one single direction. The one single direction may correspond to the correct or actual direction of the fluid flow. In this case, the correct or actual direction of the fluid flow can be unambiguously determined. Thus, in this case, the control unit may be adapted to determine, from the measured quantity of the fluid flow, information indicating the correct or actual direction of the fluid flow in two dimensions.

The term at least a range of directions of the fluid flow may relate to two or more direction candidates (candidates of directions) lying within the range of directions.

The two or more direction candidates may comprise the correct or actual direction of the fluid flow. In this case, an approximation or estimation of the correct or actual direction of the fluid flow can be determined. This approximation or estimation may be specified more accurately by appropriate measures or configurations as explained in more detail below. Thus, in this case, the control unit may be adapted to determine, from the measured quantity of the fluid flow, information indicating a range of directions of the fluid flow, the range of directions including the correct or actual direction of the fluid flow in two dimensions.

In this way, a space-saving solution is achieved. The two-dimensional sensor arrangement according to the first aspect includes displaced sensors that are arranged in parallel rather than displaced sensors that are arranged orthogonally to each other. The sensors' output is then processed in such a way that bi-dimensional flow information can be derived. Bi-dimensional (flow) information may be understood as (flow) information with only two values, e.g. one value for one direction, respectively.

This configuration solves the current limitation of the state of the art, because if, for example, the two sensors were displaced and arranged in parallel to a longitudinal direction of a catheter, it may improve the bi-dimensional fluid flow velocity measurement, which was limited by cases in which two perpendicular sensors were not exposed to the same flow pattern. The parallel arrangement may ensure that the sensors are exposed to at least approximately the same flow pattern.

The at least two displaced first sensors may be spaced parallel to each other. The at least two displaced first sensors may be spaced apart from each other, in particular transverse to or orthogonal to a common direction or common orientation of the at least two displaced first sensors. The common direction or common orientation of the at least two displaced first sensors may be defined by a lengthwise/longitudinal direction of each of the at least two displaced first sensors. The at least two displaced first sensors may be arranged next to each other, in particular abreast or alongside, transverse to or orthogonal to the lengthwise/longitudinal direction of each of the at least two displaced first sensors. The common direction or common orientation of the at least two displaced first sensors may be defined by the parallel arrangement of the at least two displaced first sensors.

The control unit may be adapted to determine, from the measured quantity of the fluid flow, information indicating a direction of the fluid flow in two dimensions. The determined direction may lie within the range of directions. The range of directions may comprise a first and fourth, or a second and third quadrant of a two-dimensional coordinate system of the first plane. In this case, the determined direction may lie in an area formed by a first and fourth, or a second and third quadrant of a two-dimensional coordinate system of the first plane. For example, the range of directions may correspond to the first and fourth quadrant of the two-dimensional coordinate system or to the second and third quadrant of the two-dimensional coordinate system.

For example, the control unit may be adapted to determine, from the measured quantity of the fluid flow, information indicating a direction of the fluid flow in two dimensions, wherein the information may indicate that the direction lies in an area formed by a first and fourth, or a second and third quadrant of a two-dimensional coordinate system of the first plane.

The quadrants may be defined by a two-dimensional coordinate system comprising x- and y-axes, wherein the sensors are arranged in parallel to the y-axis. The coordinate system is not part of the sensor arrangement, but can be regarded as a virtual reference used herein to describe the direction of the fluid flow in the coordinate system. The quadrants of the two-dimensional coordinate system may be described as follows.

In geometry, the axes of a two-dimensional Cartesian system divide the plane into four infinite regions, called quadrants, each bounded by two half-axes. These quadrants are often numbered from first to fourth and denoted by Roman numerals: I (where the signs of the two coordinates are (+,+)), II (−,+), III (−,−), and IV (+,−). When the axes are drawn according to the mathematical custom, the numbering goes counter-clockwise starting from the upper right ("northeast") quadrant.

In other words, the first quadrant may be established by positive values of x and y, the second quadrant may be drawn up by a positive value of y and a negative value of x, the third quadrant may be drawn up by negative values of x and y and the fourth quadrant may be drawn up by a negative value of y and a positive value of x. The combination of the first and fourth quadrant may form the right half of the coordinate system and the second and third quadrant may form the left half of the coordinate system.

In consequence, the information indicating at least the range of directions of the fluid flow may indicate a distinction between right and left half of the sensor arrangement with respect to the y-axis of the coordinate system. The first quadrant of the two-dimensional coordinate system may be described by a respective angle $0 \leq \alpha \leq 90°$ of the coordinate system starting at the positive x-axis ($\alpha=0°$) rotating in a counter-clockwise direction or the incidence angle $180° \geq \vartheta \geq 90°$ (the incidence angle normally starts on the negative side of the x-axis and rotates clockwise). The second quadrant of the two-dimensional coordinate system may be described by a respective angle $90° \leq \alpha \leq 180°$ of the coordinate system starting at the y-axis ($\alpha=90°$) rotating in a counter-clockwise direction or the incidence angle $90° \geq \vartheta \geq 0°$. The third quadrant of the two-dimensional coordinate system may be described by a respective angle $180° \leq \alpha \leq 270°$ of the coordinate system starting at the negative x-axis ($\alpha=180°$) rotating in a counter-clockwise direction or the incidence angle $360° \geq \vartheta \geq 270°$. The fourth quadrant of the two-dimensional coordinate system may be described by a respective angle $270° \leq \alpha \leq 360°$ of the coordinate system starting at the negative y-axis ($\alpha=270°$) rotating in a counter-clockwise direction or the incidence angle $270° \leq \vartheta \leq 180°$.

The information regarding the indication of at least a range of directions of the fluid flow may indicate a trend of the direction of the fluid flow in a certain region, e.g. one or more quadrants as explained above.

The first sensors of the sensor arrangement according to the first aspect may be thermal sensors or flow sensors, for example hot wire, hot plate, constant temperature or constant current anemometers. Thermal sensors may be referred to as temperature sensors and flow sensors may be referred to as anemometric sensors.

The sensor arrangement according to the first aspect may further comprise at least two displaced second sensors, i.e. at least two second sensors that are displaced from one another. The at least two displaced second sensors may be arranged in parallel in the first plane and may be adapted to measure the quantity of the fluid flow. The at least two displaced second sensors may be spaced parallel to each other. The at least two displaced second sensors may be spaced apart from each other, in particular transverse to or orthogonal to the common direction or common orientation of the at least two displaced first sensors. The common direction or common orientation of the at least two displaced second sensors may be defined by the lengthwise/longitudinal direction of each of the at least two displaced first sensors. Each of the at least two displaced first sensors may be arranged next to one of the at least two displaced second sensors, in particular abreast or alongside, transverse to or orthogonal to the lengthwise/longitudinal direction of each of the at least two displaced first sensors. The common direction or common orientation of the at least two displaced second sensors may be defined by the parallel arrangement of the at least two displaced first sensors. The control unit may be adapted to determine the information indicating at least the range of directions of the fluid flow in two dimensions by further considering the quantity of the fluid flow measured by the at least two displaced second sensors. In other words, the control unit may further be adapted to determine, from the measured quantity of the fluid flow (as measured by the first and second sensors), the information indicating at least the range of directions of the fluid flow in two dimensions.

For example, the control unit may be adapted to determine, by further considering the quantity of the fluid flow measured by the at least two displaced second sensors, the information indicating the direction of the fluid flow in two dimensions, wherein the direction lies in the first, second, third or fourth quadrant of the two-dimensional coordinate system of the first plane. In other words, the control unit may further be adapted to determine, from the measured quantity of the fluid flow (as measured by the first and second sensors), information indicating the direction of the fluid flow in two dimensions, wherein the direction lies in the first, second, third or fourth quadrant of the two-dimensional coordinate system of the first plane. In this way, the information regarding the indication of at least the range of directions of the fluid flow may indicate a more accurate trend of the direction of the fluid flow in a certain region, e.g. one or more quadrants as explained above.

The at least two displaced second sensors may have a different size and/or length than the at least two displaced first sensors. For example, the at least two displaced second sensors may be shorter or longer in size and/or length than the at least two displaced first sensors. The term size may relate to the size in the longitudinal direction of the respective sensor.

The sensor arrangement according to the first aspect may further comprise at least two displaced third sensors, i.e. at least two third sensors that are displaced from each other. The at least two displaced third sensors may be arranged in parallel in a second plane, perpendicular to the first plane, and adapted to measure the quantity of the fluid flow. The at least two displaced third sensors may be spaced parallel to each other. The at least two displaced third sensors may be spaced apart from each other, in particular transverse to or orthogonal to a common direction or common orientation of the at least two displaced third sensors. The common direction or common orientation of the at least two displaced third sensors may be defined by a lengthwise/longitudinal direction of each of the at least two displaced third sensors.

The at least two displaced third sensors may be arranged next to each other, in particular abreast or alongside, transverse to or orthogonal to the lengthwise/longitudinal direction of each of the at least two displaced third sensors. The common direction or common orientation of the at least two displaced third sensors may be defined by the parallel arrangement of the at least two displaced third sensors. The control unit may be further adapted to determine information indicating at least a range of directions of the fluid flow in three dimensions by further considering the quantity measured by the at least two third sensors.

The sensor arrangement may further comprise at least two displaced fourth sensors arranged in parallel to the third sensors in the second plane. The at least two fourth sensors may have a different size and/or length than the at least two third sensors. The at least two displaced fourth sensors may be spaced parallel to each other. The at least two displaced fourth sensors may be spaced apart from each other, in particular transverse to or orthogonal to the common direction or common orientation of the at least two displaced third sensors. The common direction or common orientation of the at least two displaced fourth sensors may be defined by the lengthwise/longitudinal direction of each of the at least two displaced third sensors. Each of the at least two displaced third sensors may be arranged next to one of the at least two displaced fourth sensors, in particular abreast or alongside, transverse to or orthogonal to the lengthwise/longitudinal direction of each of the at least two displaced third sensors. The common direction or common orientation of the at least two displaced fourth sensors may be defined by the parallel arrangement of the at least two displaced third sensors. In this respect, the fourth sensors may be considered to correspond to the second sensors and the third sensors may be considered to correspond to the first sensors.

The at least two displaced first, second, third and/or fourth sensors of the sensor arrangement may be arranged in parallel to each other.

The measured quantity of the fluid flow may comprise or be a velocity of the fluid flow, an acceleration of the fluid flow or the like.

The velocity of the fluid flow may be determined by a lookup table, an analytical solution and/or a numerical solution of the heat transfer convection governing equation.

According to a second aspect, a catheter is provided. The catheter comprises a sensor arrangement according to the first aspect, wherein the sensor arrangement is arranged on the catheter for measuring a fluid flow, e.g. the blood flow.

The sensor arrangement may be arranged in longitudinal direction of the catheter. In this arrangement the at least two first sensors may lie parallel to the longitudinal direction of the catheter.

In this way, the space required by the sensor arrangement in the longitudinal direction on the catheter can be reduced. The perpendicular sensor arrangement of the state of the art requires more space in the longitudinal direction of the catheter, as one sensor has to be placed, in the longitudinal direction of the catheter, next to the other, perpendicular sensor. On the contrary, the sensor arrangement according to the first aspect requires less space in the longitudinal direction of the catheter, namely space at least similar to or corresponding to the length of one sensor.

The catheter may comprise or be formed as a tube. In this case, the longitudinal direction may be the longitudinal direction of the tube.

In the following, the present disclosure will further be described with reference to exemplary embodiments illustrated in the Figures, in which.

In the following description, for purposes of explanation and not limitation, specific details are set forth, such as specific sensor and geometry details, in order to provide a thorough understanding of the present disclosure. It will be apparent to one skilled in the art that the present disclosure may be practiced in other embodiments that depart from these specific details. For example, even if the present disclosure is described with reference to specific angles to illustrate directions of the fluid flow, the present disclosure may be practiced with all angles (0° to and including 360°). All of the calculations described herein may be carried out by a suitable control unit (mentioned above) e.g. using individual hardware circuitry, using software functioning in conjunction with a programmed microprocessor or a general purpose computer, using an Application Specific Integrated Circuit (ASIC) and/or using one or more Digital Signal Processors (DSPs). The control unit can be suitably connected in wireless and/or wired manner to one or more sensors and one or more sensor arrangements described herein to exchange data such as measurement values. The control unit may be arranged on a catheter on which the sensor arrangement(s) described herein is/are arranged or may be arranged separately from the catheter.

Figure 1:
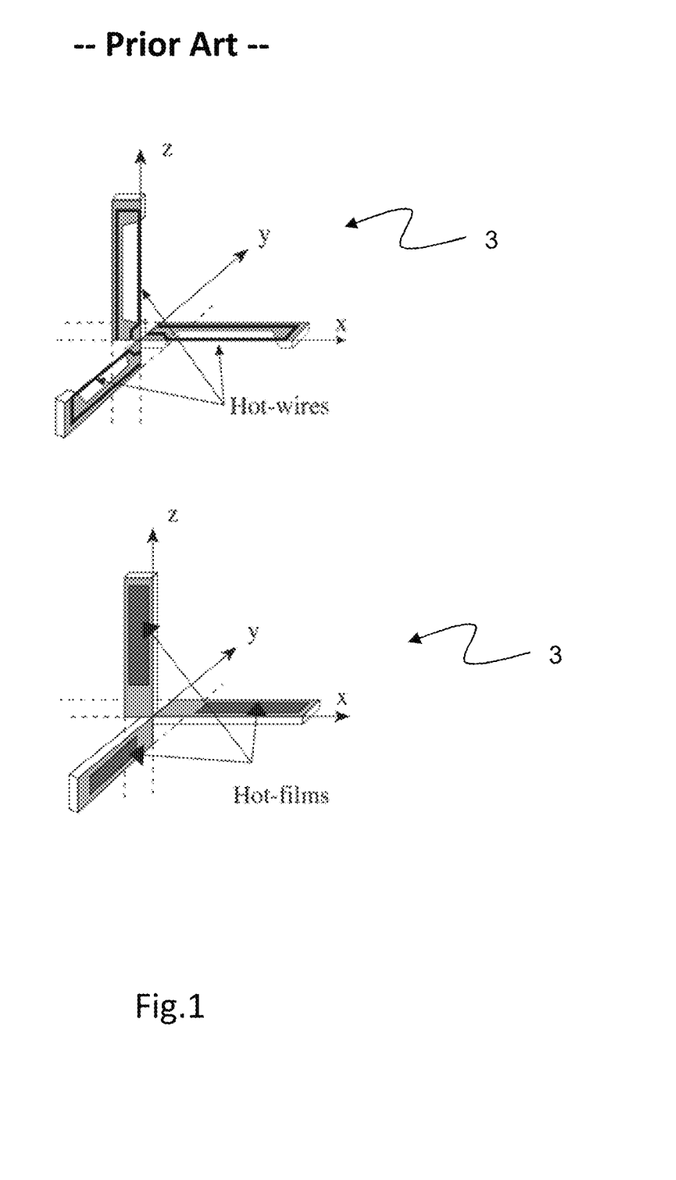
FIG. 1 is a schematic illustration of two prior art sensor arrangements.

FIG. 1 shows a schematic illustration of two prior art sensor arrangements 3 based on hot-wires and hot-films. Three orthogonal displaced sensors are shown, which are required for measuring a velocity of a three dimensional fluid flow. For the measurement of the velocity of the fluid flow in two dimensions a sensor arrangement with two orthogonal displaced sensors is required.

Figure 2A:
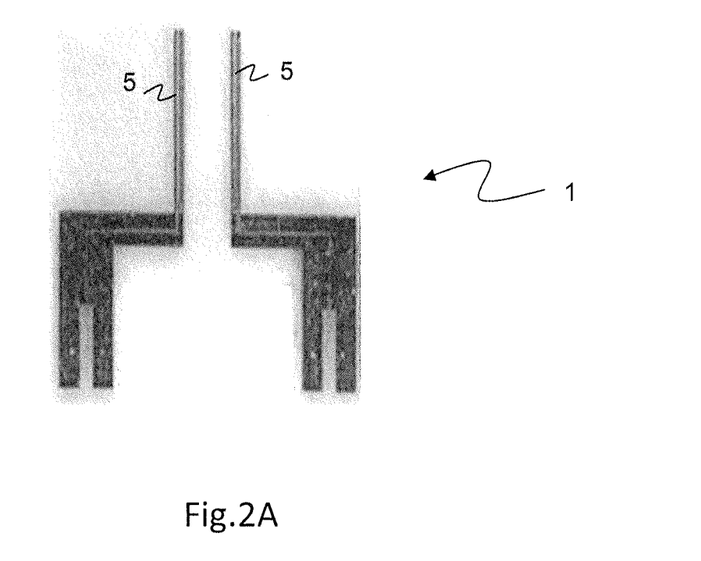
FIG. 2A is a schematic illustration of a sensor arrangement with a parallel sensor configuration.

FIG. 2A shows a schematic illustration of a sensor arrangement 1 with a parallel sensor configuration comprising two parallel sensors 5. The two sensors 5 are arranged in parallel in a common plane. In the example of FIG. 2A the sensors 5 of the sensor arrangement 1 have a rectangular geometry, but they may also be implemented as parallel wires or have a different geometry, e.g. circular or elliptical. This configuration is built to measure a direction of the fluid flow, which may be originating from the left or right of a sensor plane, as described in more detail below.

Figure 2B:
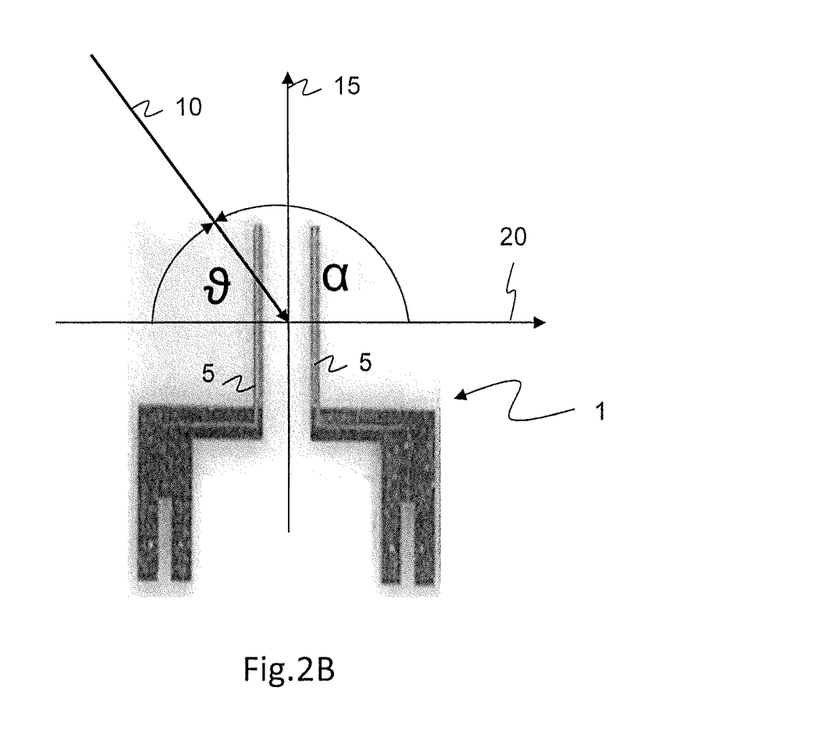
FIG. 2B is a schematic illustration of a sensor arrangement with a parallel sensor configuration and a fluid flow indication.

FIG. 2B shows a schematic illustration of the sensor arrangement 1 of FIG. 2A and a fluid flow 10 indication. The additionally indicated fluid flow 10 describes a direction having an incidence angle $\vartheta$ with respect the negative side of the x-axis 20. In this scenario, the incident fluid flow 10 is exemplarily indicated to originate from the left and thus to be on the left hand side of the sensors plane. The sensor plane is, in the present example, formed by the two axes in y-direction 15 and x-direction 20. In other words, the incident fluid flow 10 is exemplarily indicated to originate from the left hand side with respect to the y-axis 15 and to end in the origin of the coordinate system.

Figure 2C:
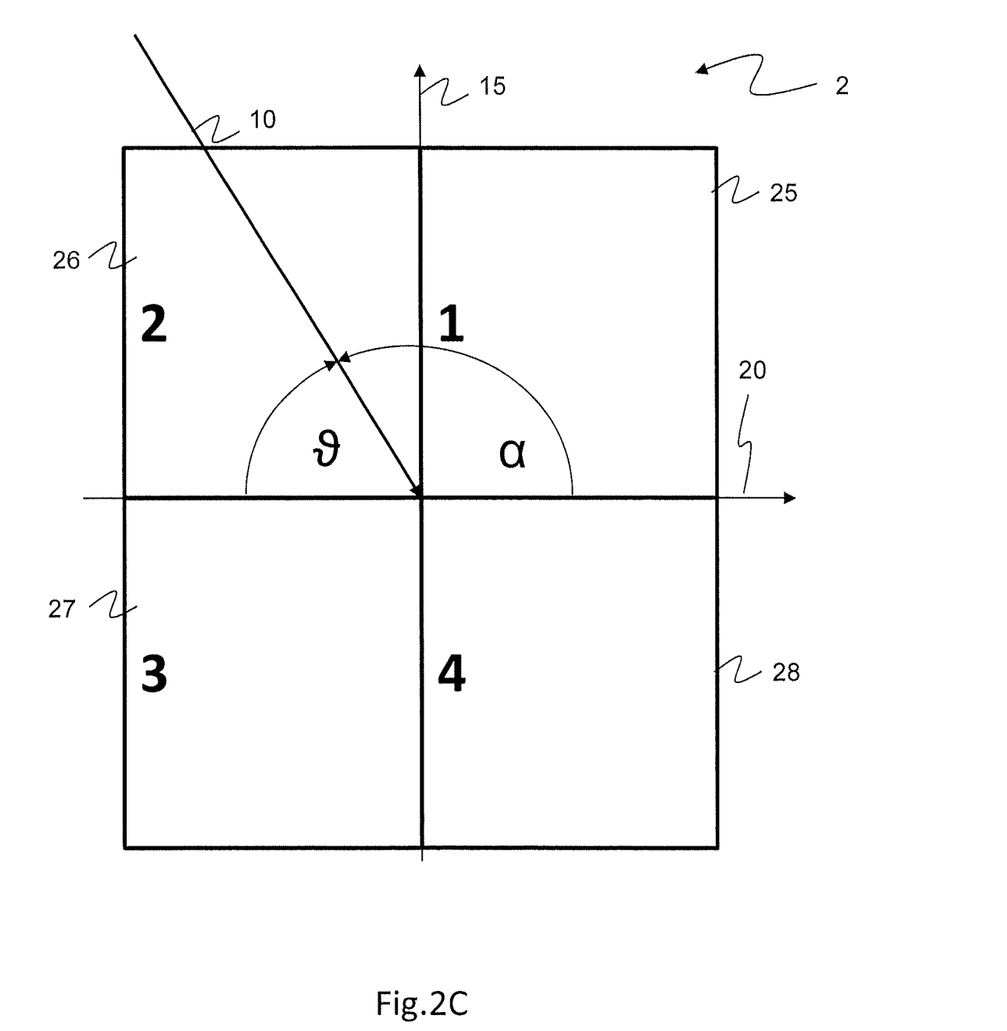
FIG. 2C is a schematic illustration of a two-dimensional coordinate system with indicated first, second, third and fourth quadrants, and an indicated fluid flow.

FIG. 2C shows a schematic illustration of a two-dimensional coordinate system 2 illustrated in FIG. 2B in more detail. That is, the two-dimensional coordinate system 2 of FIG. 2C has a first 25, a second 26, a third 27 and a fourth 28 quadrant. Further, a fluid flow 10 is indicated in the coordinate system. The sensor arrangement 1 is adapted to determine at least a range of directions of the fluid flow 10 within the coordinate system. For example, the sensor arrangement 1 may determine that the direction of the fluid flow 10 lies within one or more quadrants of the two-dimensional coordinate system 2. In the scenario of two parallel sensors 5, the information is bi-dimensional and indicates a direction coming from a left hand side or a right hand side with respect to the y-axis 15. In other words, the sensor arrangement 1 is configured to determine that the direction lies in the second 26 and third 27 quadrant (left side), or the first 25 and fourth 28 quadrant (right side), respectively. In the example of FIG. 2C, the sensor arrangement can determine, for example, that the direction of the fluid flow 10 lies within the area formed by the second quadrant 26 and third quadrant 27.

Figure 3A:
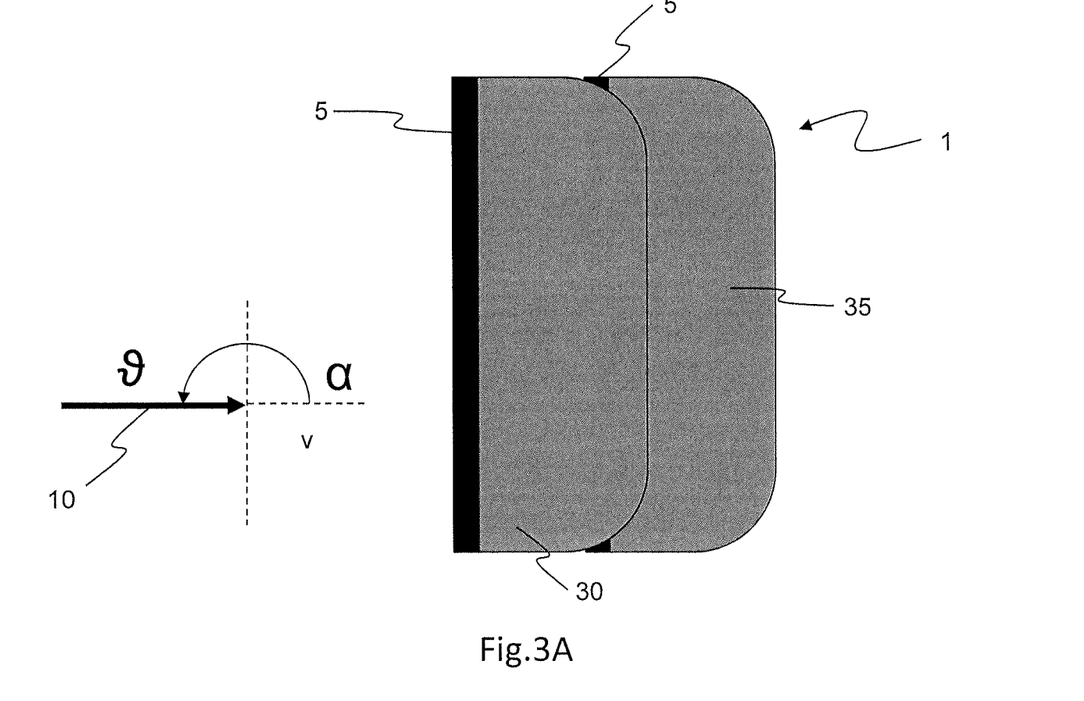
FIG. 3A is a schematic illustration of a sensor arrangement with a parallel sensor configuration and an exemplary temperature distribution, when the incidence angle of the fluid flow is $\vartheta=0°$ ($\alpha=180°$)

FIG. 3A shows a schematic illustration of further details of the sensor arrangement 1 of FIG. 2A. FIG. 3A illustrates an exemplary temperature distribution 30, 35 of the fluid, when the incidence angle of the fluid flow is $\vartheta=0°$ ($\alpha=180°$). In case of a flow (and flow velocity) with an incidence angle of $\vartheta=0°$ ($\alpha=180°$), the left sensor is working normally and is not affected by the right sensor. The right sensor measures, however, a slightly warmed fluid, as shown by the isothermal area 30, so its measurement will be of a lowered magnitude with respect to the one measured by the left sensor.

Figure 3B:
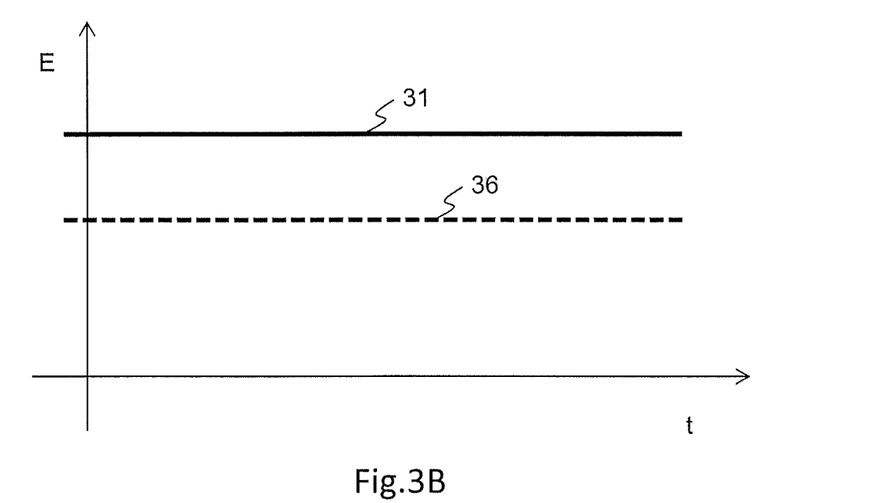
FIG. 3B is a schematic illustration of measurement values, when the incidence angle of the fluid flow is $\vartheta=0°$ ($\alpha=180°$)

FIG. 3B shows a schematic illustration of the measurement values 31, 36 measured by the sensors 5 in the example of FIG. 3A, when the incidence angle of the fluid flow is $\vartheta=0°$ ($\alpha=180°$) as illustrated in FIG. 3A. As described above with respect to FIG. 3A, the first measurement value 31 as measured by the left sensor is higher than the second measurement value 36 measured by the right sensor. As the first measurement value 31 is higher than the second measurement value 36, the sensor arrangement 1 can derive that the direction of the fluid flow lies in the second or third quadrant. There is still some ambiguity as to where exactly in the second and third quadrant the direction lies. The sensor arrangement 1 can be suitably calibrated to lower or even nullify this ambiguity. For example, the sensor arrangement 1 can be calibrated such that the difference between the measurement values 31, 36 is a maximum difference value when the incidence angle of the fluid flow is $\vartheta=0°$ ($\alpha=180°$). Thus, when determining measurement values 31, 36 and thus deriving a difference value between these measurement values 31, 36, the sensor arrangement sensor 1 can detect that the determined difference value corresponds to the calibrated maximum difference value. Thus, the sensor arrangement 1 can determine that the direction of the fluid flow is along the x-axis 20 without knowing whether the direction is pointing into the left or right direction. By further considering whether the left or right sensor returned the lower measurement value, the sensor arrangement 1 can further determine whether the direction is pointing into the left of right direction. If the left sensor returns the higher measurement value 31, then the sensor arrangement 1 determines that the direction points to the right $\vartheta=0°$ ($\alpha=180°$), i.e. the fluid flow is from left to right. If the left sensor returns the lower measurement value 36, then the sensor arrangement 1 determines that the direction points to the left $\vartheta=180°$ ($\alpha=0°$), i.e. the fluid flow is from right to left.

Figure 3C:
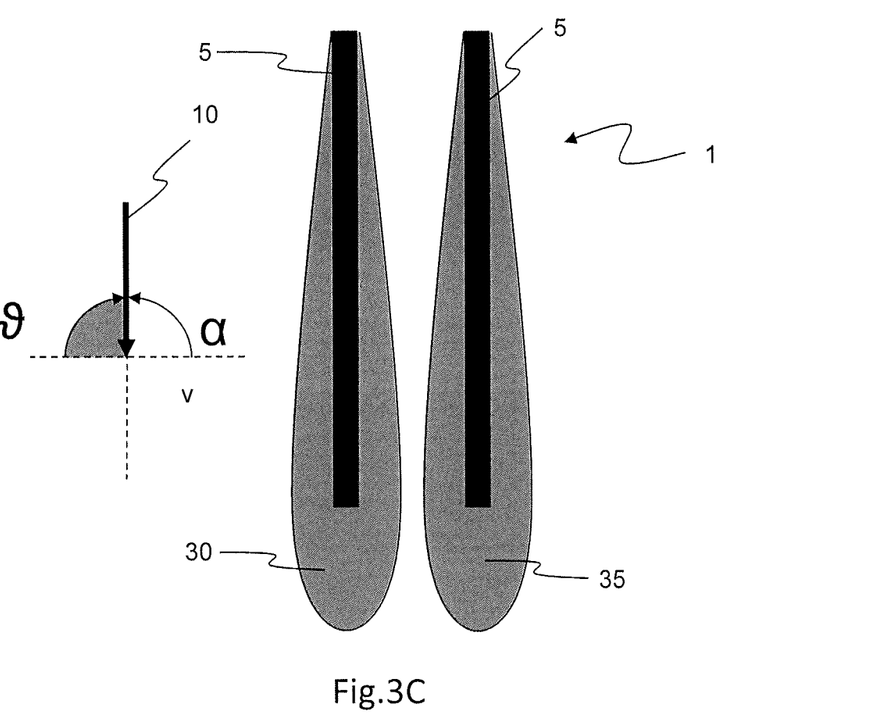
FIG. 3C is a schematic illustration of a sensor arrangement with a parallel sensor configuration and an exemplary temperature distribution, when the incidence angle of the fluid flow is $\vartheta=90°$ ($\alpha=90°$)

FIG. 3C shows a schematic illustration of the sensor arrangement 1 of FIG. 2A. FIG. 3C further shows an exemplary temperature distribution 30, 35, when the incidence angle of the fluid flow is $\vartheta=90°$ ($\alpha=90°$). The left sensor and the right sensor are either not affecting each other or they are affecting each other in an equal manner, which depends on the distance between the sensors 5 and the magnitude of the flow velocity.

Figure 3D:
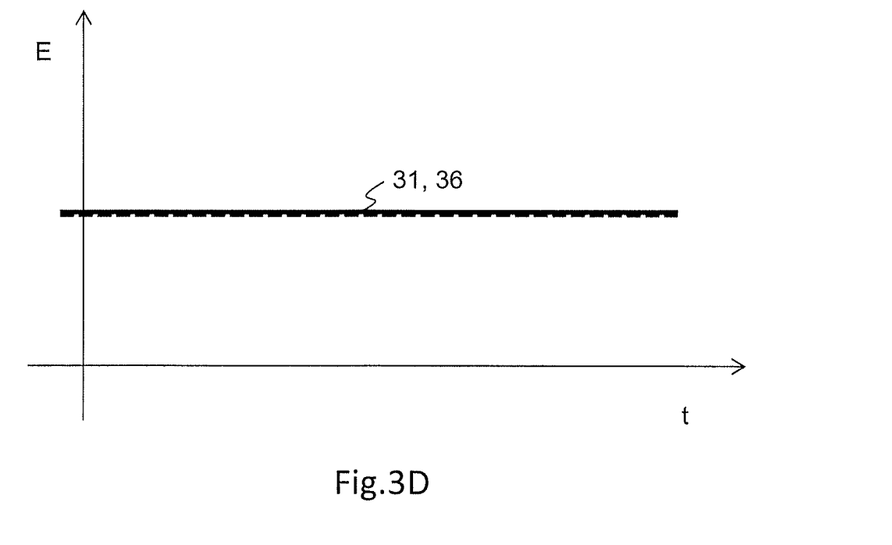
FIG. 3D is a schematic illustration of measurement values, when the incidence angle of the fluid flow is $\vartheta=90°$ ($\alpha=90°$)

FIG. 3D shows a schematic illustration of the measurement values 31, 36 measured by the sensors 5 in the example of FIG. 3C, when the incidence angle of the fluid flow is $\vartheta=90°$ ($\alpha=90°$). In this case, both sensors 5 return the same measurement values 31, 36. Thus, the sensor arrangement 1 can derive, as the sensors 5 are either not affected by each other or affected in an equal manner, that the direction of the fluid flow is along the y-axis 15, e.g. either up or down in this illustration. Since this scenario usually describes the primary direction in a catheter comprising a sensor arrangement arranged in longitudinal direction of the catheter, the direction indicates the usual blood flow.

Figure 3E:
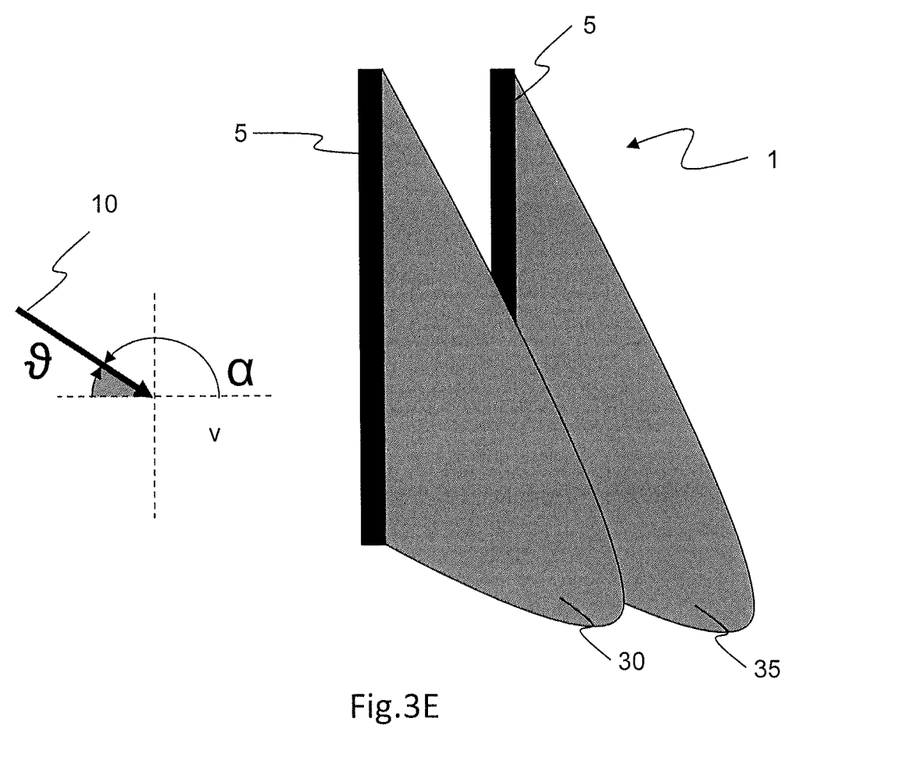
FIG. 3E is a schematic illustration of a sensor arrangement with a parallel sensor configuration and an exemplary temperature distribution, when the incidence angle of the fluid flow is $\vartheta=30°$ ($\alpha=150°$)

FIG. 3E shows a schematic illustration of the sensor arrangement 1 of FIG. 2A. FIG. 3E further illustrates an exemplary temperature distribution 30, 35, when the incidence angle of the fluid flow is $\vartheta=30°$ ($\alpha=150°$). The left sensor is affecting the measurement of the right sensor similar to the case of $\vartheta=0°$ ($\alpha=180°$). However, the difference between the measurement values 31, 36 of the two sensors 5 is lower because the influence of the left sensor will affect only a part of the area of the right sensor.

Figure 3F:
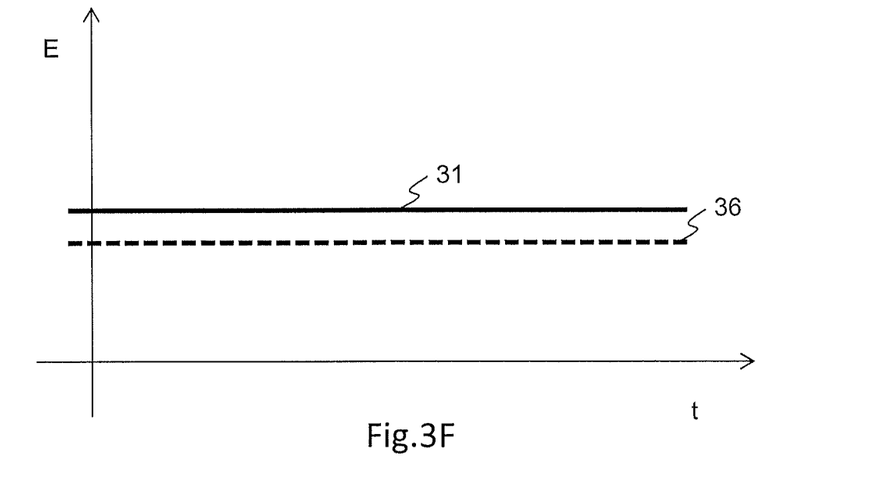
FIG. 3F is a schematic illustration of measurement values, when the incidence angle of the fluid flow is $\vartheta=30°$ ($\alpha=150°$)

FIG. 3F shows a schematic illustration of the measured difference 31, 36, when the incidence angle of the fluid flow is $\vartheta=30°$ ($\alpha=150°$). As explained above with respect to FIGS. 3A and 3B, the sensor arrangement 1 determines, by comparing the measurement values 31, 36, that the direction lies in the second or third quadrant in the example of FIG. 3E. There is remaining ambiguity regarding the distinction between the second or third quadrant. Also in this case the effect described above with respect to FIGS. 3A and 3B will be present, i.e. the right sensor will be less sensible to the fluid flow due to the influence of the left sensor on the right sensor. In other words, the left sensor will return the higher measurement value 31. However, the difference between the measurement values 31, 36 is lower than in FIG. 3B, as the right sensor is influenced less by the left sensor than in FIG.

3A. If the sensor arrangement is suitably calibrated as explained above, it can determine that the direction is in the second or third quadrant, but not on the x-axis 20.

Figure 3G:
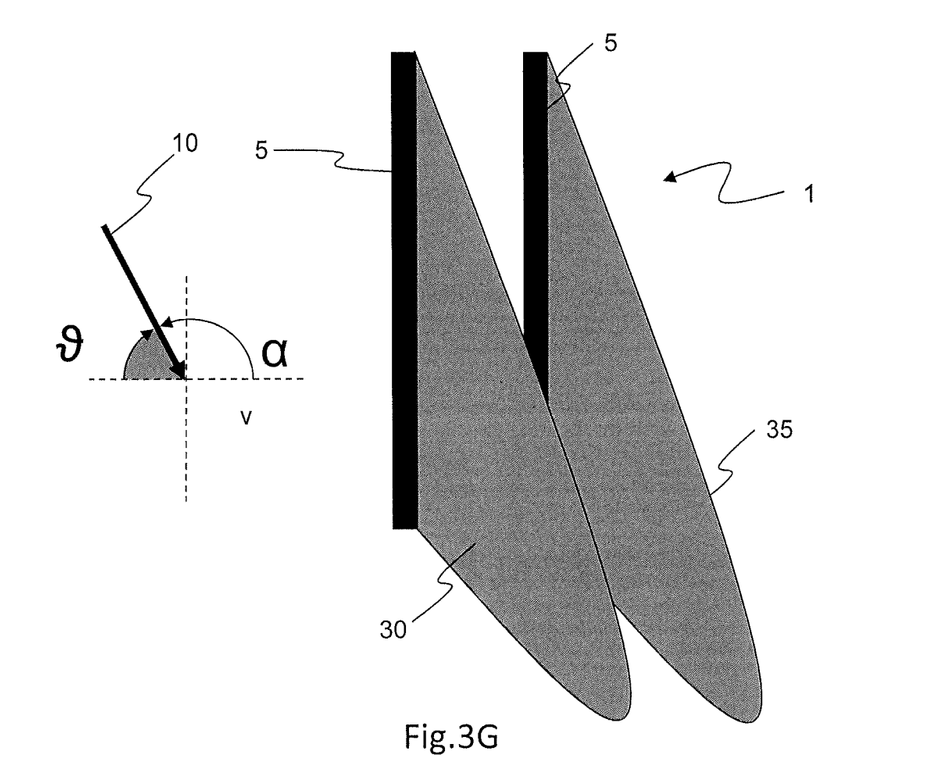
FIG. 3G is a schematic illustration of a sensor arrangement with a parallel sensor configuration and an exemplary temperature distribution, when the incidence angle of the fluid flow is $\vartheta=60°$ ($\alpha=120°$)

FIG. 3G shows a schematic illustration of the sensor arrangement 1 of FIG. 2A. Further, FIG. 3G shows an exemplary temperature distribution 30, 35, when the incidence angle of the fluid flow is $\vartheta=60°$ ($\alpha=120°$). Again, the left sensor is affecting the measurement of the right sensor similar to the case of $\vartheta=0°$ ($\alpha=180°$) and $\vartheta=30°$ ($\alpha=150°$). However, the difference between the measurement values 31, 36 of the two sensors 5 is lower than in the other two cases because the influence of the left sensor will affect only a smaller part of the area of the right sensor.

Figure 3H:
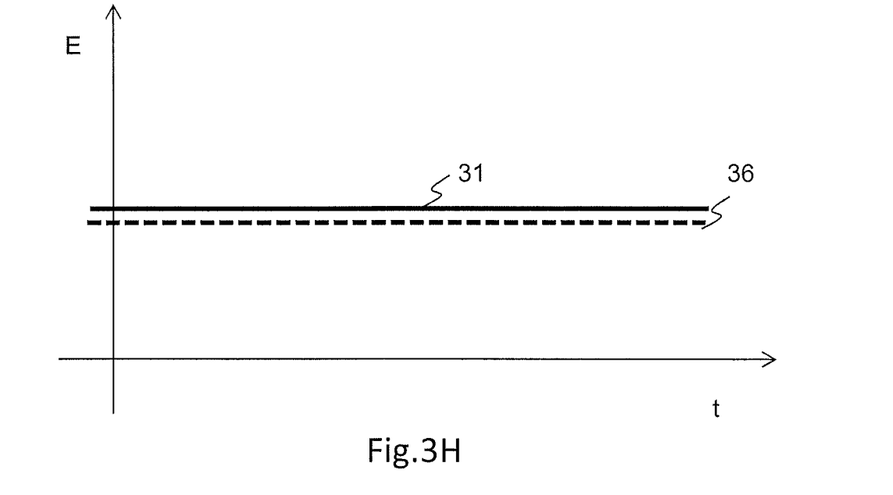
FIG. 3H is a schematic illustration of measurement values, when the incidence angle of the fluid flow is $\vartheta=60°$ ($\alpha=120°$)

FIG. 3H shows a schematic illustration of the measurement values 31, 36 measured by the sensors 5, when the incidence angle of the fluid flow is $\vartheta=60°$ ($\alpha=120°$). As explained above, the sensor arrangement 1 can determine that the direction lies in the second or third quadrant, because the left sensor returned the higher measurement value 36. There remains the ambiguity as to where exactly the direction lies within the second or third quadrant. If suitably calibrated in the way explained above, the sensor arrangement 1 may even determine that the direction of the fluid is closer to the y-axis 15 than in the case of $\vartheta=30°$ ($\alpha=150°$) as the difference between the measurement values 31, 36 is smaller.

Figure 4:
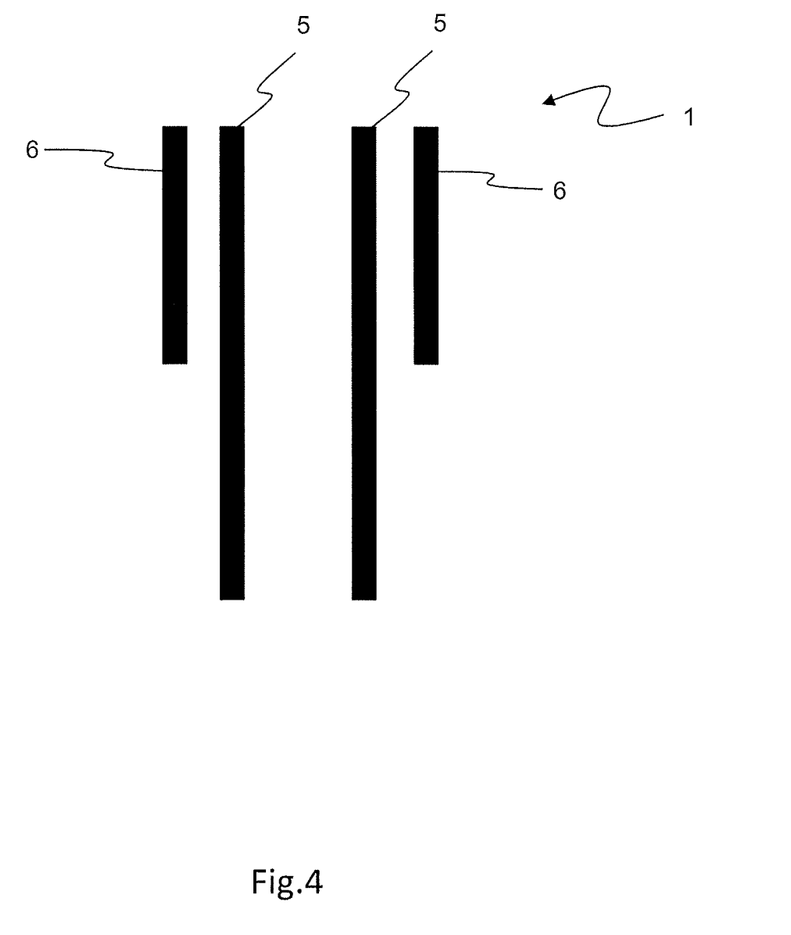
FIG. 4 is a schematic illustration of a sensor arrangement with a parallel sensor configuration and two additional parallel sensors.

FIG. 4 shows a schematic illustration of the sensor arrangement 1 having the parallel sensor configuration comprising the two parallel sensors 5 as illustrated in FIGS. 2A to 3H and explained above and two additional parallel sensors 6. This configuration allows distinguishing between the first, second, third and fourth quadrant of a two-dimensional plane, wherein the two parallel sensors 5 and the additional two parallel sensors 6 are aligned in parallel in the same plane. The disambiguation between $0° \leq \vartheta \leq 90°$ (second quadrant, $180° \geq \alpha \geq 90°$ and $270° \leq \vartheta \leq 360°$ (third quadrant, $270° \geq \alpha \geq 180°$ is performed by adding the two parallel sensors 6 for example as an anemometric sensor or a temperature sensor, respectively.

If the two parallel sensors 6 are anemometric sensors, and:
  if the right sensor of the two sensors 6 records a lower value with respect to the left sensor of the two sensors 6, it means that the sensor is working in the region $270° \leq \vartheta \leq 360°$ ($270° \geq \alpha \geq 180°$);
  if the left sensor of the two sensors 6 records an equal value with respect to the right sensor of the two sensors 6, and the flow is going from left to right as determined by the sensors 5, then it means that the direction is in the region $0° \leq \vartheta \leq 90°$ ($180° \geq \alpha \geq 90°$);
  if both left and right sensors of the two sensors 6 record a reduced fluid flow velocity with respect to the normal fluid flow velocity measured by the left and right sensor of the two sensors 5, it means that the flow is going in the direction of $\vartheta=270°$ ($\alpha=270°$); and
  if both left and right sensors of the two sensors 6 record an equal fluid flow velocity with respect to the normal fluid flow velocity measured by the left and right sensors of the two sensors 5, it means that the flow is going in the direction of $\vartheta=90°$ ($\alpha=90°$).

If the two parallel sensors 6 are temperature sensors, and:
  if the right sensor of the two sensors 6 records a higher value with respect to the left sensor of the two sensors 6, then the sensor is working in the region $0° \leq \vartheta \leq 90°$ ($180° \geq \alpha \geq 90°$);
  if the left sensor of the two sensors 6 records an equal value with respect to the right sensor of the two sensors 6, and the flow is going from left to right as determined by sensors 5, then it means that the direction is in the region $270° \leq \vartheta \leq 360°$ ($270° \geq \alpha \geq 180°$);
  if both left and right sensors of the two sensors 6 record a higher temperature with respect to the fluid temperature than the sensors 5, it means that the flow is going in the direction of $\vartheta=270°$ ($\alpha=270°$); and
  if both left and right sensors 6 record an equal temperature with respect to the fluid temperature as sensors 5, it means that the flow is going in the direction of $\vartheta=90°$ ($\alpha=90°$).

Similarly, the disambiguation between $180° \geq \vartheta \geq 90°$ (first quadrant, $0 \leq \alpha \leq 90°$) and $270° \geq \vartheta \geq 180°$ (fourth quadrant, $270° \leq \alpha \leq 360°$) can be performed.

Figure 5A:
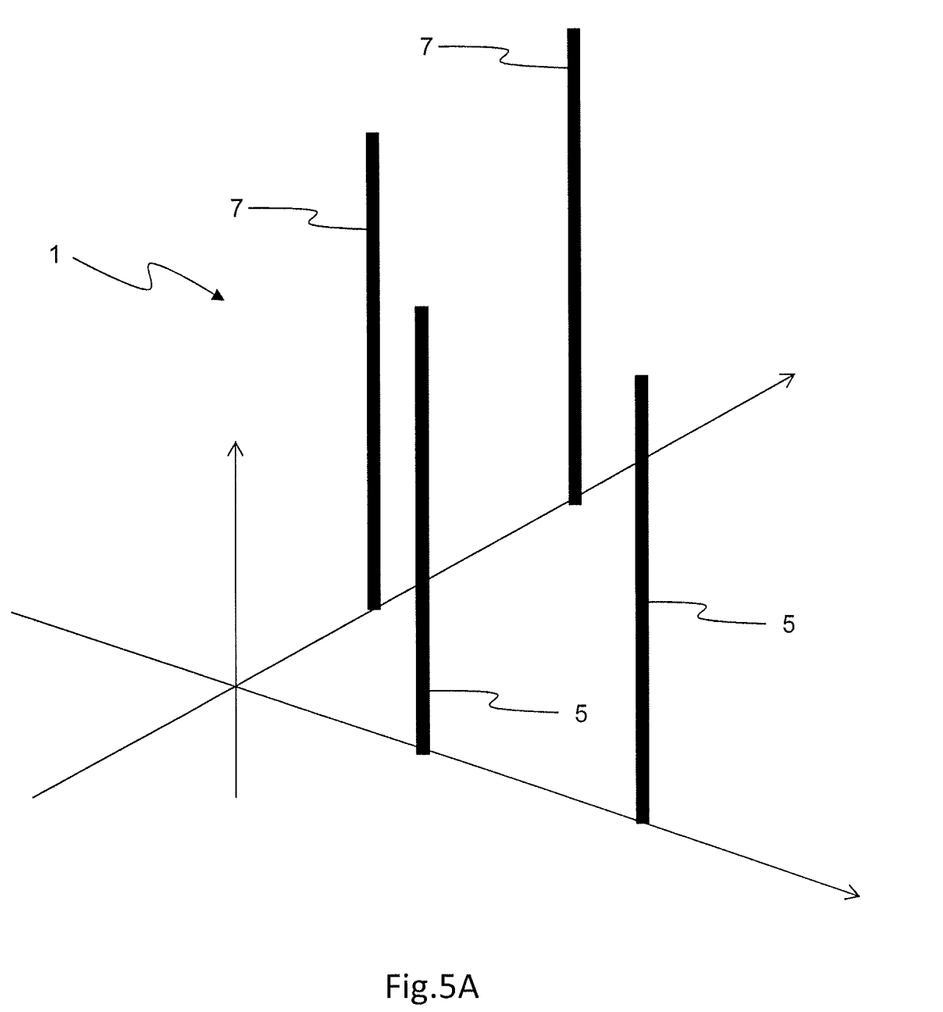
FIG. 5A is a schematic illustration of a sensor arrangement for a fluid flow measurement in three dimensions.

FIG. 5A shows a schematic illustration of a sensor arrangement 1 for a fluid flow measurement in three dimensions with first sensors 5 and second sensors 7, wherein the sensors 5, 7 are arranged in parallel, but the first sensors 5 and the second sensors 7 are placed along two non-parallel axes, e.g. two perpendicular axes as illustrated in FIG. 5A, whereby a three-dimensional information according to a direction of the fluid flow can be gathered.

Figure 5B:
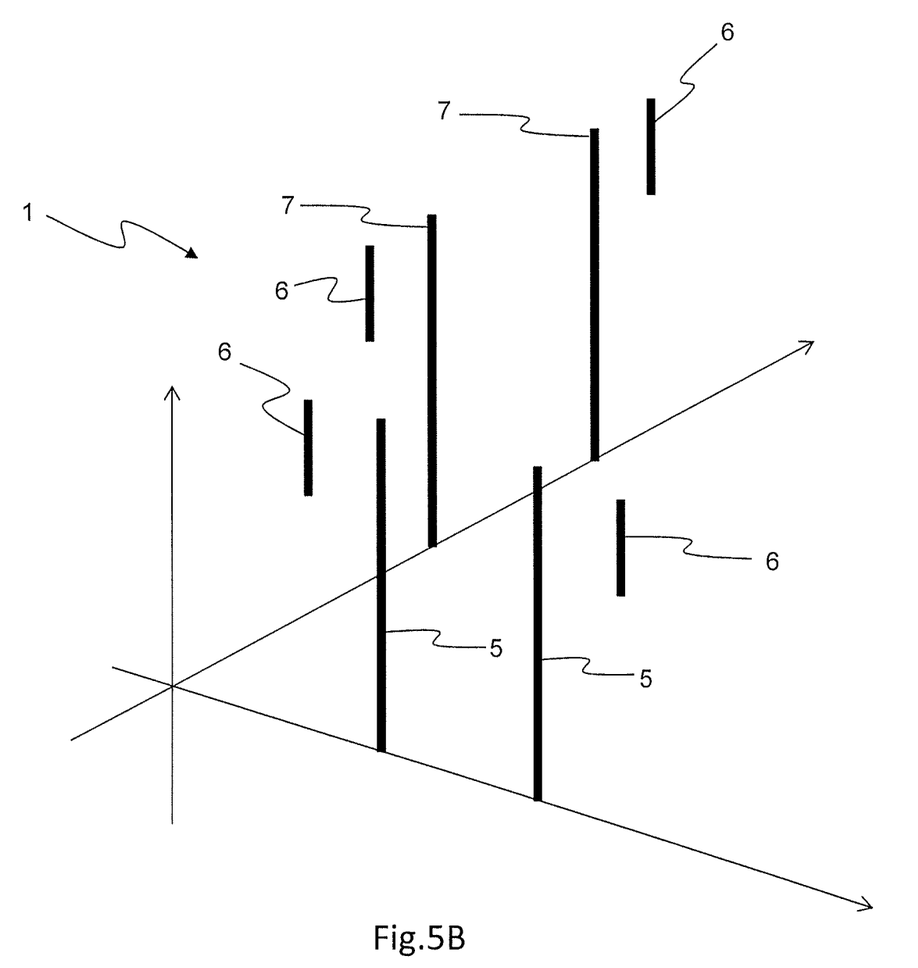
FIG. 5B is a schematic illustration of a sensor arrangement for a fluid flow measurement in three dimensions with additional sensors.

FIG. 5B shows a schematic illustration of a sensor arrangement 1 for a fluid flow measurement in three dimensions, wherein additional sensors 6 are added to the sensor arrangement 1 of FIG. 5A to more precisely gather information regarding the three-dimensional case as explained above with respect to FIG. 4. This extension may lead to information indicating a direction, which correspond to octants of a three-dimensional coordinate system.

Figure 6:
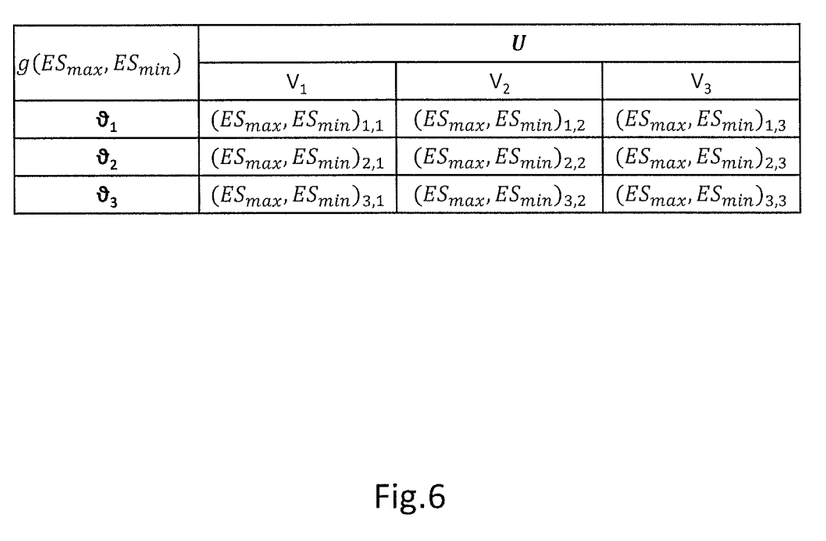
FIG. 6 is a schematic illustration of an example lookup table for solving the heat transfer convection governing equation.

FIG. 6 shows a schematic illustration of an example lookup table for solving the heat transfer convection governing equation in order to implement the concept of comparing measurement values to derive the fluid flow direction as explained above. When a moving fluid with temperature $T_f$ encounters a warmer body at a temperature $T_s$, there is a heat transfer between the two bodies known as convective heat transfer. The governing equation of this physical phenomenon is:

$$\rho c \left[ \frac{\partial T}{\partial t} + v_i \frac{\partial T}{\partial x_i} \right] - \frac{\partial}{\partial x_i}\left(k \frac{\partial T}{\partial x_i}\right) - q = 0$$

Where T is the temperature, q is the volumetric heat source, $\rho$ is the material's density, k the thermal conductivity, c the specific heat. $v_i$ is the fluid's velocity in direction $\chi_i$. The equation describes the temperature distribution into a fluid domain where the fluid is moving.

The convective effect is used for building anemometers, a resistive sensor $R_s$ is heated at a temperature $T_s$ above fluid's temperature $T_f$ and the power transferred to the fluids by the sensor, when the fluid is moving, is described by the following equation:

$$I^2 R_s = h A_s (T_s - T_f)$$

where I is the current flowing into the sensor, h is a convective coefficient and $A_s$ is the area of the sensor. Anemometric sensors are also sensitive to the direction of the fluid with respect to the geometrical dimension of the sensor.

If the two measurements of S1 (left sensor) and S2 (right sensor) are defined as:
  $ES_{min}$ is the value measured by the sensor (S1 or S2) measuring the lower value, and
  $ES_{max}$ is the value measured by the sensor (S1 or S2) measuring the higher value.

The following equation may be written:

$$ES_{max} = f_k(U_{eff}),$$

where $f_k$ is a function that relates the measured velocity with an electrical output of the sensor, e.g. the well-known King's Law. In a bi-dimensional space the "effective cooling velocity" or Ueff is defined as:

$$U_{eff}^2 = U^2(\cos \vartheta^2 k^2 \sin \vartheta^2)$$

This equation describes the relation between a measured $U_{eff}$ with the real fluid's velocity U, where $\vartheta$ is the angle (orientation of the velocity) between the sensor's transverse direction and the fluid's velocity and k is a sensor's coefficient (geometrical coefficient specific for each sensor) that quantifies a sensor's sensibility to the velocity direction perpendicular to the main direction.

The measurement performed by the $S_{min}$ (sensor (S1 or S2) measuring the lower value) may be in general written as:

$$ES_{min} = f_{FSmax}(v, \vartheta) - f_{shade}(v, \vartheta, T_s)$$

where $f_{shade}$ is the function describing the loss in sensitivity of the sensor S measuring the lower value that is a function of the fluid's velocity, the velocity orientation and the known sensor's temperature ($T_s$). By coupling the measurements $ES_{max}$ and $ES_{min}$, it is possible to establish a relationship between the two measurements that may identify the two values of v and $\vartheta$, when $0° \leq \vartheta \leq 90°$ ($180° \geq \alpha \geq 90°$) or $270° \leq \vartheta \leq 360°$ ($270° \geq \alpha \geq 180°$) (FIG. 3A-3H), assuming that the flow goes from the left sensor to the right sensor (the system behaves symmetrically when the flow goes from the right sensor to the left sensor).

A function g $$[v, \vartheta] = g(ES_{max}, ES_{min})$$

may be formulated using different methods:
Empirical definition, through test bench experiments. In this case, g is then formulated as a look up table;
Analytical solution of the heat transfer convection governing equation;
Numerical solution of the heat transfer convection governing equation; or
Use of reduced and simplified formulas derived from the heat transfer convection governing equation.

The invention claimed is:

1. A sensor arrangement comprising:
a first pair of sensors arranged in parallel in a first two dimensional plane, the first pair of sensors including a first sensor and a second sensor, said first and second sensors extending in a longitudinal direction corresponding to a first (y) axis of said plane and extending parallel next to each other but spaced apart from one another along a second (x) axis of said plane, and said first sensor being adapted to perform a first measure a quantity of a fluid flow measurement that provides a first measurement value, said second sensor being adapted to perform a second fluid flow measurement that provides a second measurement value, said first and second sensors being longer in said longitudinal direction than in a second direction perpendicular to said longitudinal direction, said second direction corresponding to the second (x) axis of said plane; and
a control unit adapted to determine, from a difference between the first measurement value and the second measurement value, information indicating a direction of the fluid flow in said first two dimensional plane, wherein the first sensors are hot wire, hot plate, constant temperature or constant current anemometers.

2. The sensor arrangement according to claim 1, wherein the information indicates that the direction lies in an area formed by a first and fourth, or a second and third quadrant of a two-dimensional coordinate system of the first two dimensional plane.

3. The sensor arrangement of claim 2, wherein the sensor arrangement is calibrated to provide a maximum difference between the first and second measurement values when a direction of fluid incidence on said first and second sensors is at an angle of zero with respect to the second (x) axis.

4. The sensor arrangement according to claim 1, further comprising a second pair of sensors, said second pair of sensors including third and fourth sensors extending in the longitudinal direction corresponding to the first (y) axis of said plane and extending parallel to each other but at a second distance from each other, said third sensor being adapted to perform a third fluid flow measurement that provides a third measurement value, said fourth sensor being adapted to perform a fourth fluid flow measurement that provides a fourth measurement value, said third and fourth sensors being longer in said longitudinal direction than along the second (x) axis of said plane; and
wherein the control unit is adapted to determine the information indicating the direction of the fluid flow in two dimensions by further considering the third and fourth measurement values measured by the third and forth sensors respectively.

5. The sensor arrangement according to claim 4, wherein the third and fourth sensors have a different shape or are a different size from said first and second sensors and wherein said second distance is greater than a first distance by which said first and second sensors are separated in said second direction.

6. The sensor arrangement of claim 5, wherein said first, second third and forth sensors are part of a one dimensional sensor array with the first, second, third and fourth sensors being arranged parallel to each other in a row which extends in said second direction perpendicular to the longitudinal direction of the first, second, third and fourth sensors.

7. The sensor arrangement of claim 6, wherein the sensor arrangement is calibrated to provide a maximum difference between the first and second measurement values when a fluid direction of fluid incidence angle is zero with respect to the second (x) axis.

8. The sensor arrangement according to claim 1, further comprising at least two displaced third sensors arranged in parallel in a second plane, perpendicular to the first plane, and adapted to measure a quantity of the fluid flow, wherein the control unit is further adapted to determine information indicating at least a range of directions of the fluid flow in three dimensions by further considering the quantity of the fluid flow measured by the at least two displaced third sensors.

9. The sensor arrangement according to claim 1, further comprising:
a second pair of sensors, said second pair of sensors including third and fourth sensors extending in the longitudinal direction corresponding to the first (y) axis of said plane and extending parallel to each other but at a second distance from each other.

10. The sensor arrangement according to claim 1, wherein the sensor arrangement measures a velocity of the fluid flow.

11. The sensor arrangement according to claim 10, wherein the velocity of the fluid flow is determined by a lookup table, an analytical solution or a numerical solution of the heat transfer convection governing equation.

* * * * *